United States Patent
Amundson et al.

(10) Patent No.: US 6,895,281 B1
(45) Date of Patent: May 17, 2005

(54) INDUCTIVE COIL APPARATUS FOR BIO-MEDICAL TELEMETRY

(75) Inventors: Mark D. Amundson, Cambridge, MN (US); Richard E. Stindt, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/541,452

(22) Filed: Mar. 31, 2000

(51) Int. Cl.$^7$ .............................................. A61N 1/08
(52) U.S. Cl. ............................................ 607/60; 607/32
(58) Field of Search ........................... 607/30, 32, 33, 607/60, 61, 59; 340/870.31, 573.1; 128/903, 899

(56) References Cited

U.S. PATENT DOCUMENTS

| | | | | |
|---|---|---|---|---|
| 4,134,408 A | * | 1/1979 | Brownlee et al. | 128/419 PS |
| 4,361,153 A | | 11/1982 | Slocum et al. | 128/419 |
| 4,416,283 A | | 11/1983 | Slocum | 128/419 |
| 4,494,545 A | | 1/1985 | Slocum et al. | 128/419 |
| 4,542,532 A | | 9/1985 | McQuilkin | 455/78 |
| 4,586,508 A | | 5/1986 | Batina et al. | 128/419 PG |
| 4,681,111 A | | 7/1987 | Silvian | 128/419 |
| 4,700,707 A | * | 10/1987 | Batina et al. | 128/419 |
| 5,016,634 A | | 5/1991 | Vock et al. | 128/419 |
| 5,313,953 A | | 5/1994 | Yomtov et al. | 128/696 |
| 5,342,408 A | | 8/1994 | deCoriolis et al. | 607/32 |
| 5,476,488 A | | 12/1995 | Morgan et al. | 607/30 |
| 5,626,630 A | | 5/1997 | Markowitz et al. | 607/60 |
| 5,683,432 A | | 11/1997 | Goedeke et al. | 607/32 |
| 5,741,315 A | * | 4/1998 | Lee et al. | 607/60 |
| 5,814,089 A | * | 9/1998 | Stokes et al. | 607/32 |
| 5,843,139 A | | 12/1998 | Goedeke et al. | 607/32 |
| 5,861,019 A | | 1/1999 | Sun et al. | 607/60 |
| 5,882,300 A | | 3/1999 | Malinouskas et al. | 600/300 |
| 5,948,006 A | | 9/1999 | Mann | 607/61 |
| 5,949,155 A | * | 9/1999 | Tamura et al. | 307/107 |
| 5,999,857 A | | 12/1999 | Weijand et al. | 607/60 |
| 6,009,350 A | * | 12/1999 | Renken | 607/32 |
| 6,115,634 A | * | 9/2000 | Donders et al. | 607/32 |
| 6,167,312 A | * | 12/2000 | Goedeke | 607/60 |
| 6,169,925 B1 | * | 1/2001 | Villaseca et al. | 607/60 |
| 6,212,430 B1 | * | 4/2001 | Kung | 607/61 |
| 6,298,271 B1 | * | 10/2001 | Weijand | 607/60 |
| 6,301,504 B1 | * | 10/2001 | Silvian | 607/60 |
| 6,389,318 B1 | * | 5/2002 | Zarinetchi et al. | 607/71 |
| 6,400,991 B1 | * | 6/2002 | Kung | 607/61 |
| 6,424,867 B1 | * | 7/2002 | Snell et al. | 607/31 |

* cited by examiner

*Primary Examiner*—Jeffrey R. Jastrzab
*Assistant Examiner*—Frances P. Oropeza
(74) *Attorney, Agent, or Firm*—Schwegman, Lundberg, Woessner & Kluth, P.A.

(57) ABSTRACT

An improved bio-medical telemetry apparatus for programming an implanted medical device includes a large substantially planar and concentrically wound first telemetry coil. The coil is disposed inside a thin flexible housing including layers of insulative materials to prevent electrical contact between loops of the first telemetry coil and to hold the first telemetry coil formed shape in place. The apparatus further includes a communication lead coupled to the first telemetry coil for communicating with a medical device programmer. During a telemetry session the first telemetry coil including the flexible housing is disposed at a posterior location of the torso and an implanted medical device disposed subcutaneously on an anterior location of the torso. During programming the first telemetry coil is inductively coupled to the implanted medical device for wireless data communication with the implanted medical device. The large, substantially planar design of the first telemetry coil permits more even and large flux paths, which allow for less precise positioning of the apparatus with respect to the implanted medical device. Also, the flexible housing conforms to irregular surface of patient's and supporting furnishing providing comfort to patients lying upon the first telemetry coil during telemetry sessions.

14 Claims, 6 Drawing Sheets

INDUCTIVE COIL APPARATUS FOR BIO-MEDICAL TELEMETRY

TECHNICAL FIELD OF INVENTION

This invention relates generally to the field of implantable biomedical devices, and particularly, but not by way of limitation to an improved inductive coil apparatus for biomedical telemetry applications.

BACKGROUND

Implanted medical devices, can receive programmed instructions, and can also send back messages regarding the status of the implantable medical device. This ability to interrogate with an implantable medical device in place in a patient is called telemetry. Telemetry can provide, among other things, useful information for troubleshooting implanted medical devices. Information sent from an external programmer to the implanted medical device can be used to program parameters for performing particular functions using the implanted device. The inductively coupled telemetry signal is generally quite local, to decrease the likelihood of inappropriate alteration of the program by environmental sources of radiofrequency energy or magnetic fields.

The evolution of biomedical telemetry has led to the development of increasingly sophisticated communication between implantable devices and external programmer that provides device's therapies or monitoring capabilities. Most of these external programmers rely on detachable coil assemblies ranging in size of about 2 to 3 inches in diameter to be optimally placed (e.g., at the site of device implantation, or in front of a patient at about 2 inches or less from the site of device implantation), for optimal signaling and inductive coupling between the implanted device and the external coil. These coil assemblies are connected to the external programmer unit to convey the signaling to and from the coils. Most existing external coil assemblies are hand-held types that must be kept stationary in this optimal position during an entire session of telemetry. During a typical telemetry session at a hospital or follow-up clinic, the patient or a medical care giver holds the coil in the optimum position.

With these telemetry communication devices, a coil-to-coil inductive coupling is usually used for wireless transmission of signals. Wireless signaling of implantable device telemetry enters through the coil via inductive coupling. The external coil is inductively coupled to a telemetry coil in the implanted device. The telemetry coil within the implantable device is usually fairly small and can usually only transmit small amounts of signal power to the exterior of a patient. Thus, an existing external coil assembly connected to a device programmer must be optimally placed for best signaling and inductive coupling to obtain a reliable telemetry communication. However, this reliance on optimal placement is generally undesirable because, the patient and/or care giver may find it tiring or difficult to find the optimal position and hold the external coil in place during the entire session. Increasing demands on the telemetry system to transmit and receive more data, may require long telemetry sessions. The medical care giver may require free movement of hands to perform other tasks. Moreover, requiring the coil to be positioned over the implanted medical device may, interfere with other medical procedures associated with the implanted device. Thus, there is a need for an improved biomedical telemetry apparatus to provide telemetry communication between the external programmer and the implanted medical device even when the external coil is not optimally placed. Also, there is a need for an improved biomedical telemetry apparatus to reduce or eliminate the need to hold the coil by hand in the optimal position during the telemetry sessions.

SUMMARY

The present apparatus provides, among other things, a biomedical telemetry communication with reduced patient and/or care giver discomfort during telemetry sessions. The present apparatus is generally capable of providing telemetry communication even when a telemetry coil is non-optimally placed with respect to an implanted medical device. The present apparatus can also provide telemetry communication even when the telemetry coil is placed anywhere near or around the site of a patient's implanted medical device (e.g., even when the external coil is not held by hand and even when placed at distances of twenty (20) centimeters or more from the site of implanted medical device).

According to one embodiment, a first telemetry coil having one or more loops of a conductive wire concentrically wound in a common plane having a pre-determined outer dimension is disposed inside a flexible housing. In one embodiment, the flexible housing consists of at least one layer of insulative material to prevent electrical contact and to retain the first telemetry coil formed shape in place. In one embodiment the flexible housing is made of polyimid material. In one embodiment, the flexible housing including the first telemetry coil is hermetically sealed. In another embodiment the flexible housing is thin, flexible, and capable of conforming to irregular surfaces of a patient, and supporting furnishing without causing any discomfort to patients during telemetry sessions. A communication lead suitable for telemetry data communication, is operatively coupled to the first telemetry coil (having a reasonable length coaxial cable) on one end, and interfaces with an medical device programmer for programming an implanted medical device on the other end. Also included is an optional padded cover for the flexible housing including the first telemetry coil to provide patient comfort. In one embodiment, the padded cover includes one or more straps for attaching the first telemetry coil to the patient. In one embodiment the padded cover includes a hook-and-loop type straps for attaching the first telemetry coil to the examination furnishing. In another embodiment the optional padded cover is disposed over the flexible housing for patient comfort. The material of the first telemetry coil can be any conductive wire having low resistance.

In another embodiment, the telemetry coil includes two or more telemetry coils (e.g., a first telemetry coil and a second telemetry coil) concentrically arranged in a common plane to allow for separate transmission and reception performance needs. The first and second telemetry coils are coupled to each other to stop all but near-field magnetic flux linkages from interfering with wireless communication. In this embodiment, the first and second telemetry coils are disposed in a flexible housing to prevent electrical contact and to hold the coil formed shapes in place.

In another embodiment the communication lead includes a planarly arranged wire methods to isolate differing coil functions. Still another embodiment of the communication lead includes a multiple shielded conductors to isolate differing coil functions, to lower the complexity, and to improve performance of the cable assembly.

Large telemetry coils having an outer dimension of at least fifteen (15) centimeters or more in diameter permits better, more even magnetic flux distribution through its core of the coil loops. The larger flux paths results in larger flux aperture area allowing for less precise coil positioning relative to the patient's device and even permit the coil to be placed on the opposite side of the patient's body.

Another aspect of the invention provides, among other things, a thin and flexible housing including a telemetry coil for negligible discomfort to patients lying upon the flexible housing during telemetry sessions. The flatter design also permits the telemetry coil to be placed on the patient's table in a surgical suite, where the apparatus may remain out of the sterile field by being covered over with the normal sterile drapes currently provided.

Another aspect of the invention provides, a padded cover over the flexible housing for an added comfort to a patient during telemetry sessions. In another embodiment the padded cover is a plush and comfortable pad satisfactory for the patient's use. In another embodiment the padded cover is made of a white terry cloth having hook-and-loop type straps providing a universal system for fastening to common examination furnishings such as tables and chairs.

Advantageously, the present apparatus provides telemetry data communication between a medical device programmer and an implanted medical device, even when a telemetry coil is non-optimally placed at approximately fifteen (15) centimeters or more from the implanted medical device. The wireless signaling of the implantable medical device telemetry enters through a large, planar coil via inductive coupling. Also advantageously, the present apparatus can reduce the discomfort to a patient and/or a care giver during telemetry sessions by using a thin and flexible housing that can be placed between the back of a patient and a common examination furnishing, and thus eliminating the need to hold the coil in the optimum location during telemetry sessions.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having letter suffixes represent different instances of substantially similar components.

DETAILED DESCRIPTION

In the following detailed description, reference is made to accompanying drawings, which form a part hereof, and in which is shown by way of illustration specific embodiments in which the invention may be practiced. These embodiments are describe in sufficient detail to enable those skilled in the art to practice the invention, and it is to be understood that the embodiments may be combined, or that other embodiments may be utilized and that structural, logical, and electrical changes may be made without departing from the scope of the present invention. The following detailed description is, therefore, not to be taken in a limiting sense, and the scope of the present invention is defined by the appended claims and their equivalents. In the accompanying drawings, like numerals describe substantially similar components throughout the several views. Like numerals having different suffixes represent different instances of substantially similar components. In this document, "and/or" refers to non-exclusive "or" (e.g., "A and/or B" includes each of "A but not B," "B but not A," and, "A and B").

The present methods and apparatus will be described in applications involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, biventricular or other multi-site coordination devices, monitors, programmers and recorders.

In this document, the term "optimal location" is understood to refer to placing of the telemetry coil directly above the site of implanted device or holding the telemetry coil by hand at about five (5) centimeters or less from the site of implanted medical device. Similarly, the term "predetermined outer dimension" refers to the telemetry coil having an outer dimension of fifteen (15) centimeters or more in diameter. The term "surface area" refers to the surface area occupied by the telemetry coil when placed on an examination table or chair.

This document describes, among other things, an apparatus providing an improved communication between a medical device programmer and an implanted medical device. The apparatus provides, among other things, a reduction in patient and/or care giver discomfort during telemetry sessions. The present apparatus is also capable of providing telemetry communication even when a telemetry coil is not placed in an optimum position.

For example the present apparatus can communicate even when the telemetry coil is placed at distances greater than fifteen (15) centimeters from the site of implantation. In one embodiment, this is accomplished by using a telemetry coil of pre-determined outer dimension, concentrically wound in a common plane. This provides the necessary large flux paths to inductively couple the telemetry coil with the implanted medical device for telemetry communication. In another embodiment, the present apparatus advantageously reduces the discomfort to the patient and/or care giver during the telemetry sessions by using a thin and flexible housing and a padded cover over the telemetry coil, so that for example, the telemetry coil can be placed under a patient's back (posterior location on a torso) as the patient rests on the examining table.

Figure 1:
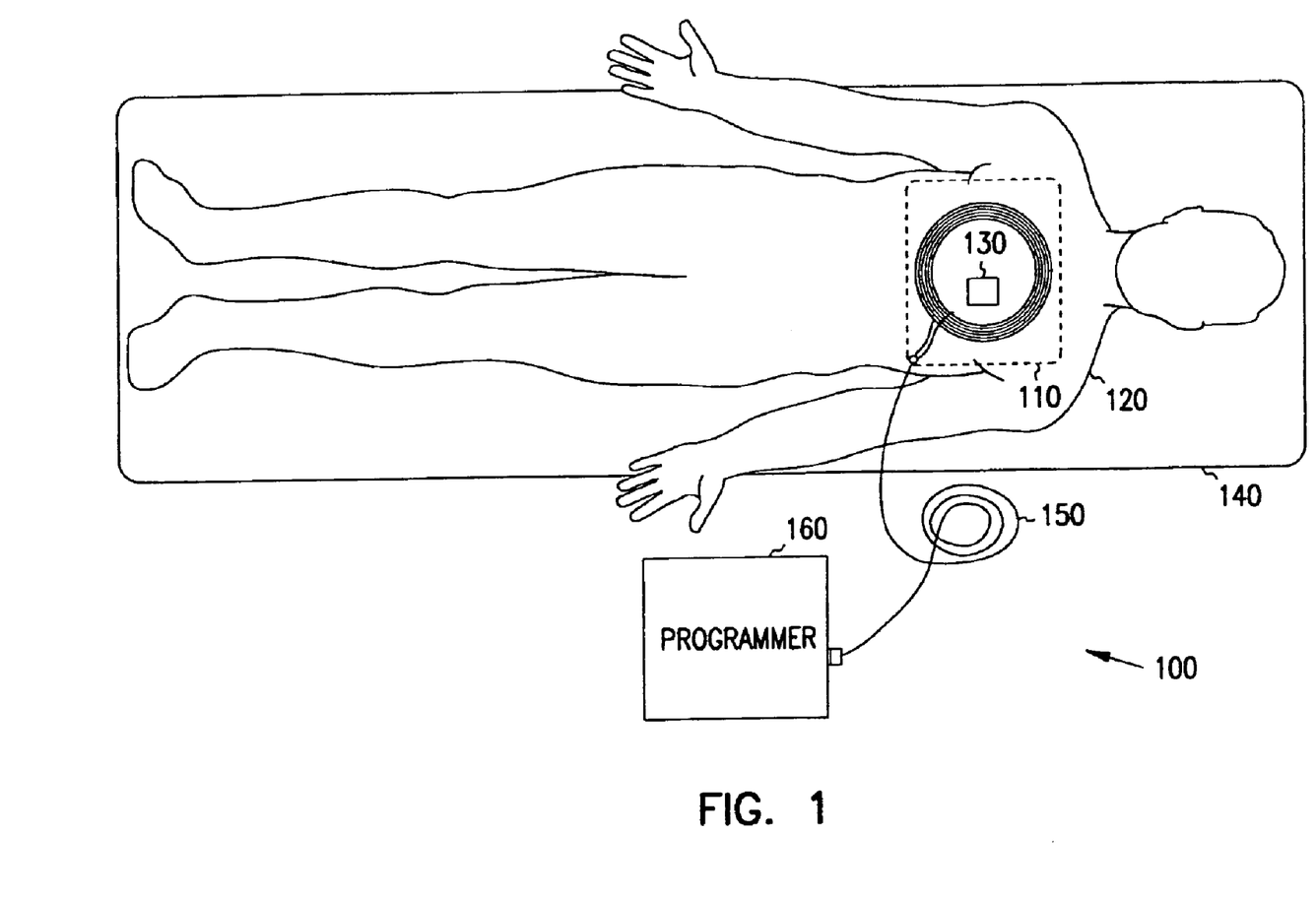
FIG. 1 is a schematic drawing illustrating generally one embodiment of portions of an apparatus and an environment in which it is used.

FIG. 1 is a schematic illustrating generally, by way of example, but not by way of limitation, one embodiment of portions of the present biomedical telemetry device and an environment in which it is used. In FIG. 1, a biomedical telemetry apparatus 100 includes, a telemetry coil assembly 110 placed under a back of a patient 120. In this example, the telemetry coil assembly 110 is located on the opposite side of the patient 120 from the implanted medical device 130, while the patient 120 is comfortably lying on an examination and/or surgical table 140. Apparatus 100 also includes a communication lead, such as, a cable assembly 150 coupled to the telemetry coil assembly 110 on a first end and interfacing with a medical device programmer 160 on a second end for communicating with the patient's implanted medical device 130.

In one embodiment, telemetry apparatus 100 is used for frequent telemetry sessions in which the apparatus can be permanently placed in the patient's dwelling for routine follow-up via trans-telephonic means. In one example, this device could be placed within the patient's supporting bed linens for casual overnight download of implantable device data.

Figure 2:
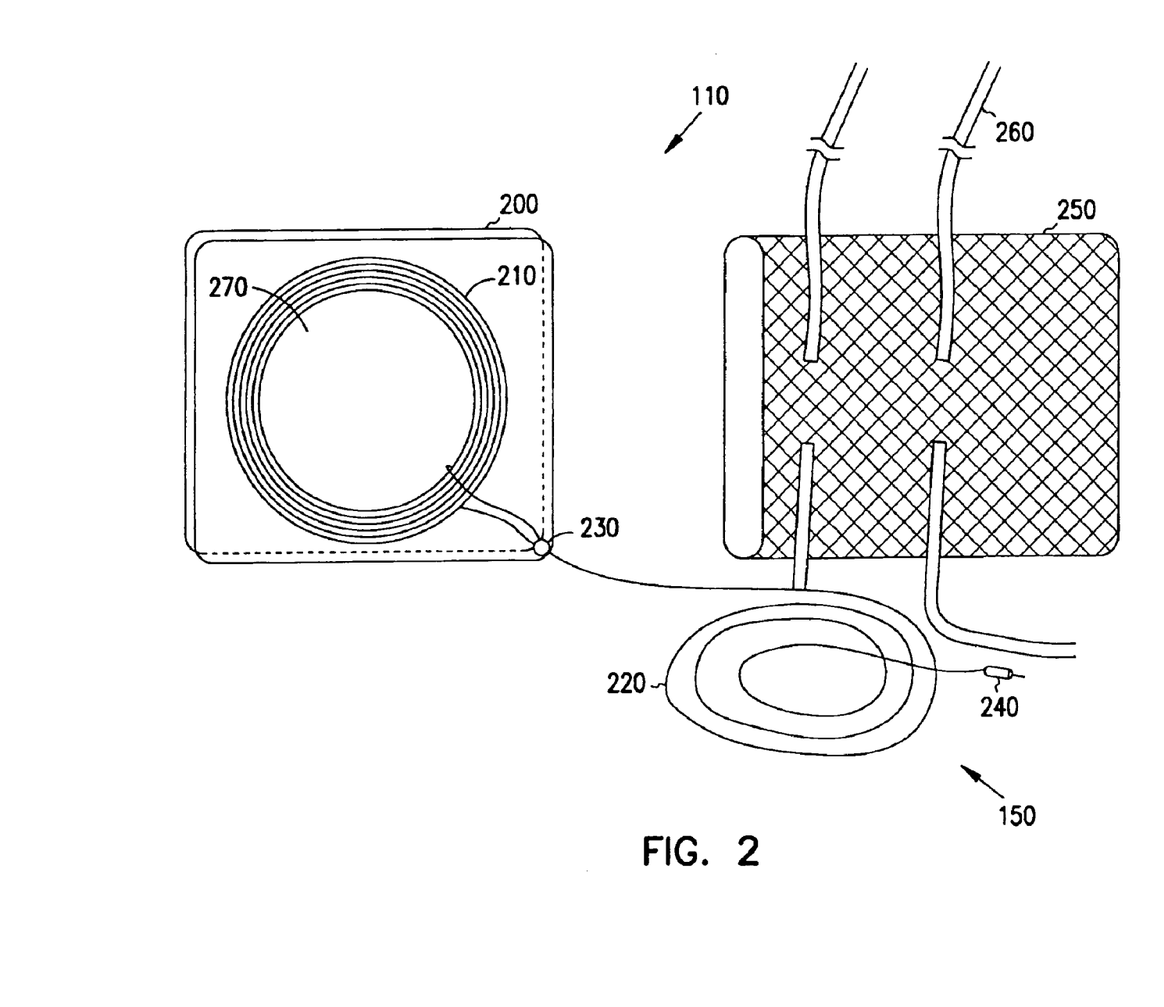
FIG. 2 is a schematic view of one embodiment of the apparatus with a padded cover placed aside and not over the apparatus.

FIG. 2 is a front view schematic, showing generally, by way of example, but not by way of limitation, one embodiment of a telemetry coil assembly 110 including a first telemetry coil 210 coupled to a communication lead, such as, a cable assembly 150. In one embodiment, the telemetry coil assembly 110 includes a thin flexible housing 200, encasing a large concentrically wound first telemetry coil 210. In one embodiment, the first telemetry coil 210 is hermetically sealed within the flexible housing 200. In another embodiment, the flexible housing is thin and capable of conforming to irregular surfaces of patients, and/or of supporting examination fixture or furnishing such fixtures and/or examination furnishings such as examination chairs and tables. Flexible housing 200 can be constructed of any insulative material capable of holding the first telemetry coil formed shape in place, and also capable of retaining its electrical properties. Flexible housing 200 can also be constructed of any moldable or layered material capable of conforming to irregular surfaces. Flexible housing can be made from Polyimid, Mylar, Acetates, and other similar materials. In one embodiment, the first telemetry coil is wound concentrically in a common plane enclosing a large surface area.

To increase advantageously the flux aperture area, the telemetry coils are wound to occupy a large surface area of approximately between one hundred seventy seven (177) to one thousand six hundred sixty one (1661) cm$^2$, which is in the range of about fifteen (15) to forty-six (46) centimeters in outside diameter. First telemetry coil 210 can include any conductive wire having low resistance and capable of providing controlled inductance. According to one aspect of the invention, the wire diameter of the first telemetry coil 210 is sized for minimal fluoroscopic imaging while providing effective low resistivity due to high frequency alternating current "skin" effect. In another embodiment, Litzendraught ("Litz") wire may be used to provide low resistivity. The need for low resistivity and controlled inductance comes from the need to increase the magneto-motive force (F) defined in units of ampere-turns or Gilberts. This, in turn, leads to increased magnetic flux through the telemetry coil aperture area. With the relatively large surface area of the telemetry coil, a more uniform flux density promotes a more controlled magnetic circuit. This provides more gradual decoupling of the mutual inductance between the apparatus 100 and an implanted medical device 130 as their displacement increases from one another. A larger first telemetry coil surface area permits more even magnetic flux distribution through the aperture area encompassed by the telemetry coil loops. Larger flux paths allow for less precise positioning relative to the implanted medical device 130. In one embodiment, this even permits the apparatus 100 to be placed on the opposite side of the patient's body (posterior location of a torso). In one embodiment, the center core 270 of the first telemetry coil 210 includes magnetically permeable material, such as, ferrite (iron oxide) powder to enhance the flux density at the core. For anterior thoracic implants, the implanted device 130 can be programmed with telemetry coil assembly 110 adjacent his or her back while comfortably seated in a chair or lying on an examination table 140. The substantially planar design of the telemetry apparatus 100 also permits the first telemetry coil 210 to be placed on a surgical table 140. This allows the telemetry apparatus 100 to remain out of the sterile field by being covered over with the typical sterile drapes that are already provided. The larger surface area of the first telemetry coil 210 allows communication in spite of fairly poor inductive coupling orientations of sleeping patients. In another embodiment, more than one telemetry coil is used in telemetry apparatus 100 for several performance features. The general shape of the first telemetry coil 210 is not critical, as long as the first telemetry coil 210 form loops of wire. The first telemetry coil 210 can be even in the form of an antenna, as long as the first telemetry coil 210 form loops of wire.

FIG. 2 also shows the cable assembly 150. In one embodiment, a communication lead such as a cable assembly 150 includes a cable 220 operatively coupled to the first telemetry coil 210 on first end 230, and an interface module 240 coupling with a medical device programmer 160 on the second end for telemetry data communication between an implanted medical device 130 and the medical device programmer 160. The cable assembly 150 can be a simple or a complex part to transport the signaling to and from the telemetry coil(s) and implantable medical device. In one embodiment, the cable 220 includes a singular coaxial cable suitable for bi-directional communication. The cable 220 capacitance may resonate with inductance of the first telemetry coil 210 to define operating frequencies and bandwidths of telemetry communication. In another embodiment, the cable 220 could embody multiple shielded conductors and/or planar wires to isolate differing telemetry coil functions within the apparatus. Another embodiment of the cable assembly 150 incorporate active circuitry located within the flexible housing 200 for receiving and transmitting energy via the telemetry coil(s) 210 for improved telemetry performance. Since the telemetry coil inductance is tuned by capacitance and resistance, it can form a part of a band-limited receiver and transmitter subsystem much like an antenna. The mechanical size of the first telemetry coil 210 can be near enough to the electrical size (wavelength) to have a radiation resistance large enough to be an antenna. Such receive and transmit circuits may encompass microelectronics similar to surface mount/hybrid packaging.

FIG. 2 also shows an optional padded cover 250 disposed over the telemetry coil assembly 110 for providing additional patient comfort during a telemetry session (to show all of the features of the telemetry coil assembly 10, the padded cover 250 is shown aside flexible housing 200 and not over it). In one example, the padded cover 250 is made of a white terry cloth or similar fabric to provide plush and comfortable feeling to patients. Also shown attached to the padded cover 250 are hook-and-loop type straps 260 to attach to common furnishings such as examination tables and/or chairs. The present method and apparatus will work in a variety of configurations and with a variety of cable connectors and interfacing devices.

Figure 3:
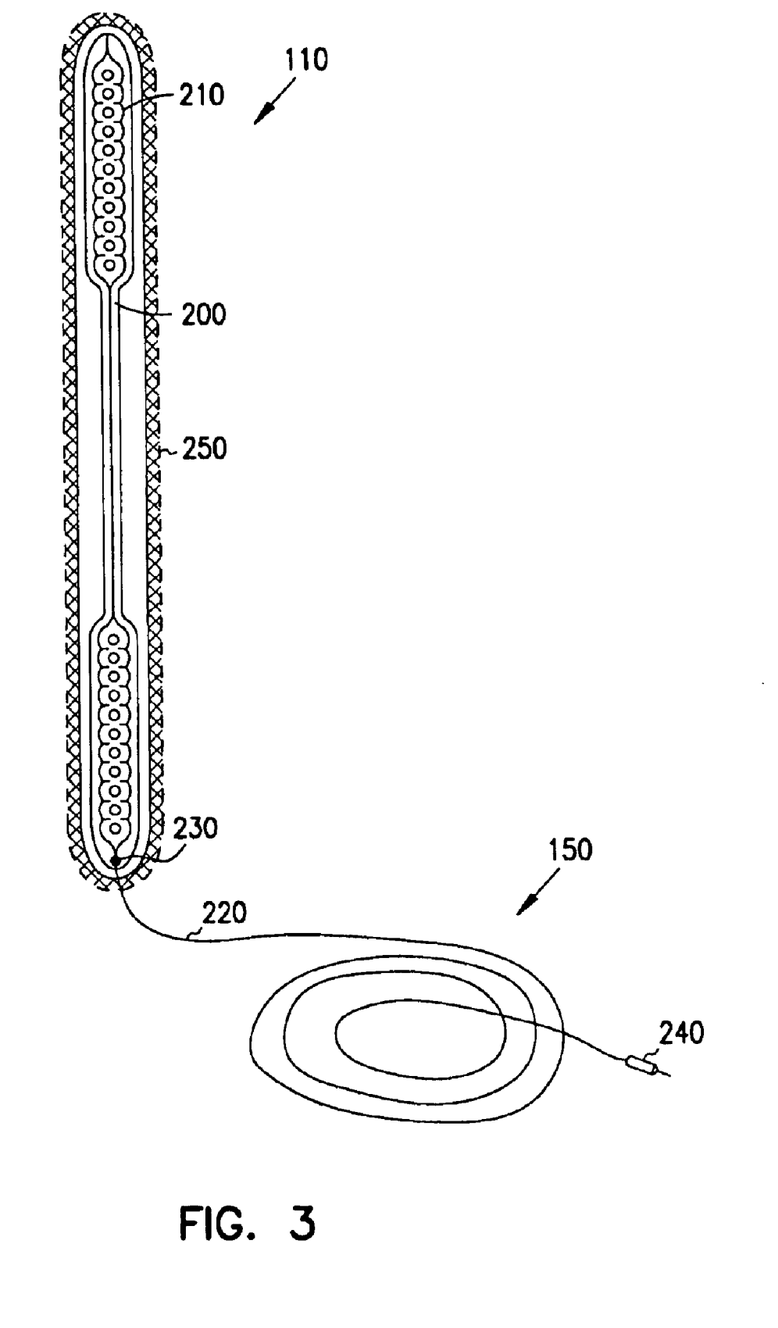
FIG. 3 is a side sectional view of one embodiment of the present subject matter showing generally a concentrically wound first telemetry coil held in place by a flexible housing with a padded cover over the flexible housing.

FIG. 3 is a sectional view illustrating generally, by way of example, but not by way of limitation, one embodiment of a first telemetry coil 210 held in place by a layered flexible housing 200. In the embodiment, as shown in FIG. 3, a telemetry coil assembly 10 includes substantially planar concentrically wound the first telemetry coil 210, captively held in place by the thin flexible housing 200. The flexible housing 200 can include many types of layered or molded materials, that provide sufficient coil support to hold the telemetry coil form in place, and also to retain its electrical properties. The flexible housing 200 can include any insulative material that does not affect telemetry coil performance and that inhibits conductivity to nearby external high voltage sources, such as cardiac defibrillation devices. In addition, the flexible housing 200 should be thin enough to avoid discomfort to a patient lying upon the telemetry coil assembly 10. In one embodiment, the telemetry coil assembly 10 is flexible enough to conform to irregular surfaces. The overall shape of the flexible housing 200 is generally not critical, however achieving the familiar shape of a personal heating pad is desired for overcoming the fears and intrusive nature of implantable device telemetry sessions. This embodiment also shows an optional padded cover 250 disposed over the flexible housing 200. FIG. 3 also shows, a communication lead such as a cable assembly 150 including a cable 220 operatively coupled to the first telemetry coil 210 at 230 on the first end, and having an interface module 240 on the second end of the cable assembly 150 for interfacing with a medical device programmer 160.

Figure 4:
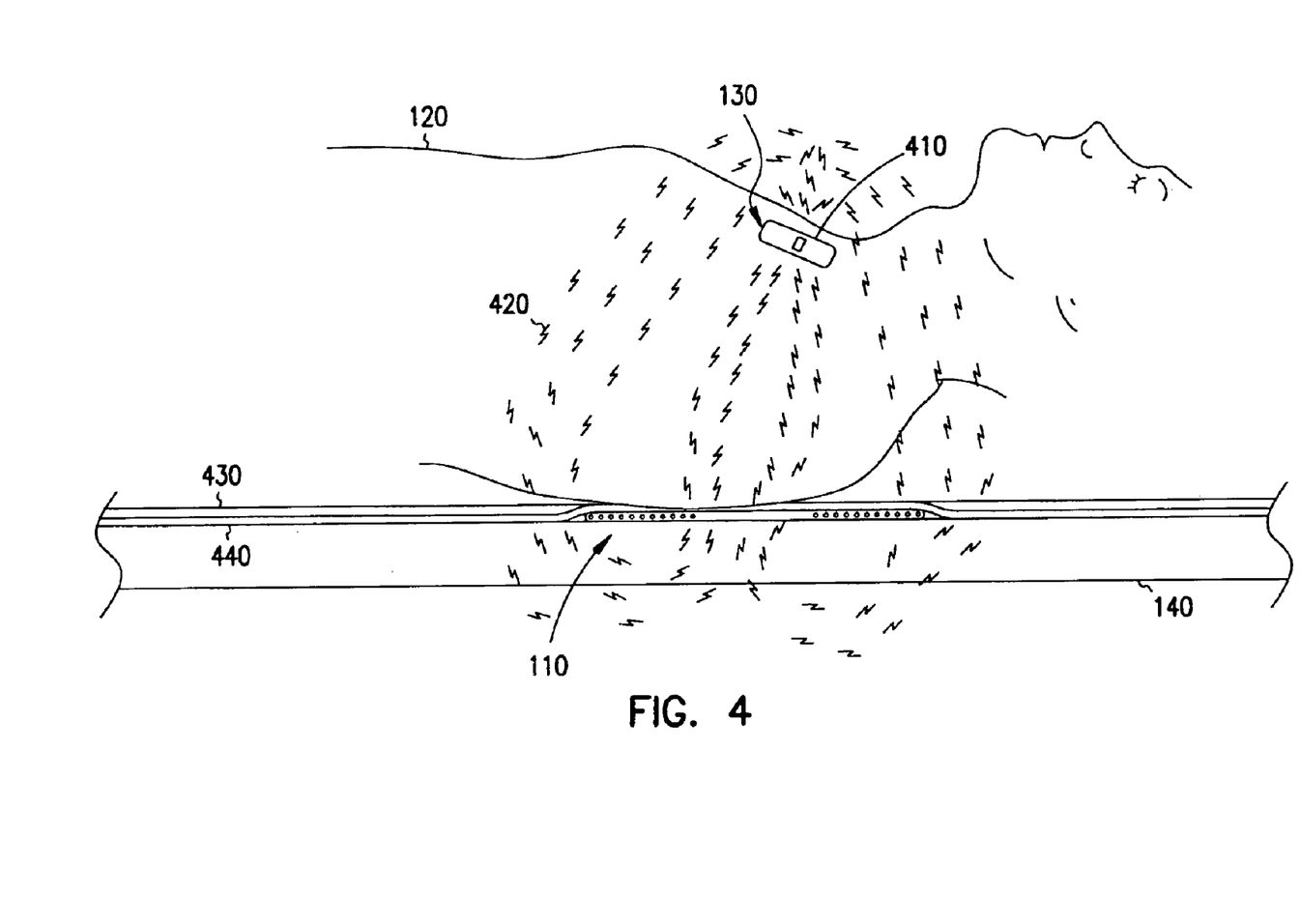
FIG. 4 is a side sectional view of one embodiment of the present subject matter showing generally the orientations of magnetic flux paths creating an inductive coupling between an implanted medical device and a first telemetry coil positioned at a posterior location on a torso (positioned under a patient's back) during a telemetry session.

FIG. 4 is a side sectional view illustrating generally, by way of example, but not by way of limitation, one embodiment of portions of apparatus 100 being used in a typical telemetry session. FIG. 4 depicts an example of orientation of the large flux paths between a telemetry coil assembly 10 including a first telemetry coil 210 and an implanted telemetry coil 410 of a patient's 120 implanted medical device 130. In this embodiment, the telemetry coil assembly 110 is shown generally disposed between the examination surgical drapes 430 and 440, and abutting the opposite side of the patient's 120 body (posterior location on a torso) while the patient 120 is laying comfortably over an examination and/or surgical table 140.

Figure 5:
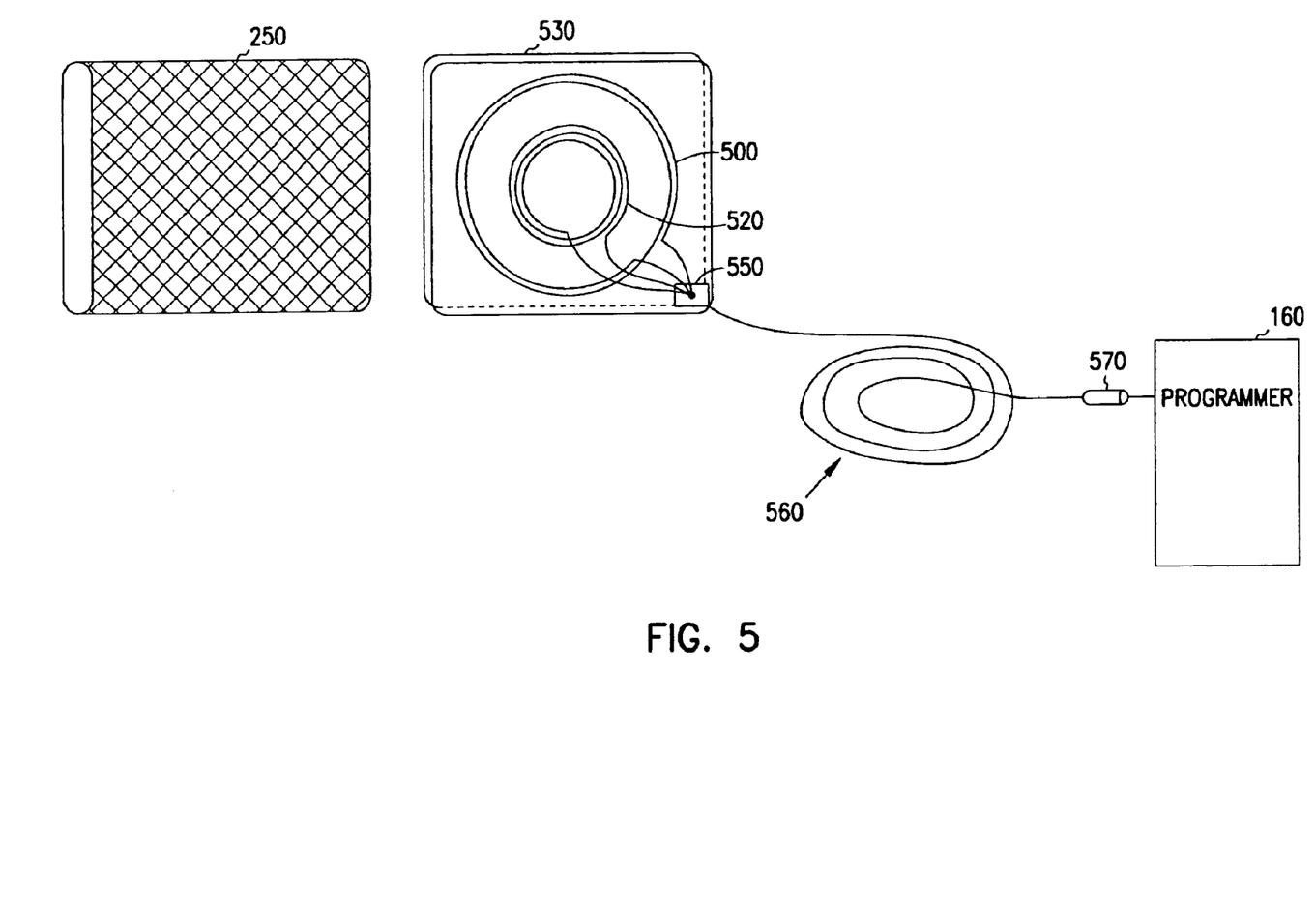
FIG. 5 is a schematic drawing of one embodiment of the present subject matter, showing generally, the utilization of multiple telemetry coils (e.g., first and second telemetry coils) in an apparatus.

FIG. 5 is a front view illustrating generally, by way of example, not by way of limitation, another embodiment of a telemetry coil assembly. FIG. 5 is similar to FIG. 2 in many respects but FIG. 5 includes, two separate concentrically wound telemetry coils 500 and 520 (e.g., first and second telemetry coils) housed in a flexible housing 530, instead of the single first telemetry coil 210 shown in FIG. 2. In this embodiment, first and second telemetry coils 500 and 520 are operatively coupled to a cable assembly 560 at 550 on first end. In one embodiment, the first and second telemetry coils 500 and 520 are arranged so that their start and finish windings are connected. This rejects far-field magnetic flux, preventing all but near-field flux linkages from interfering with wireless communication. Multiple telemetry coils also permit separate tailoring of telemetry coil parameters for bi-directional communication performance needs. Also, multiple telemetry coils may be needed to support different families of implantable devices, each with differing telemetry bandwidths and operational frequencies. Also shown in this embodiment, is the cable assembly 560 including interface module 570 on the second end to interface with a medical device programmer 160 for telemetry data communication. Also shown is an optional padded cover 250 placed aside the flexible housing 530. During telemetry sessions the padded cover 250 is placed over the flexible housing 530.

Figure 6:
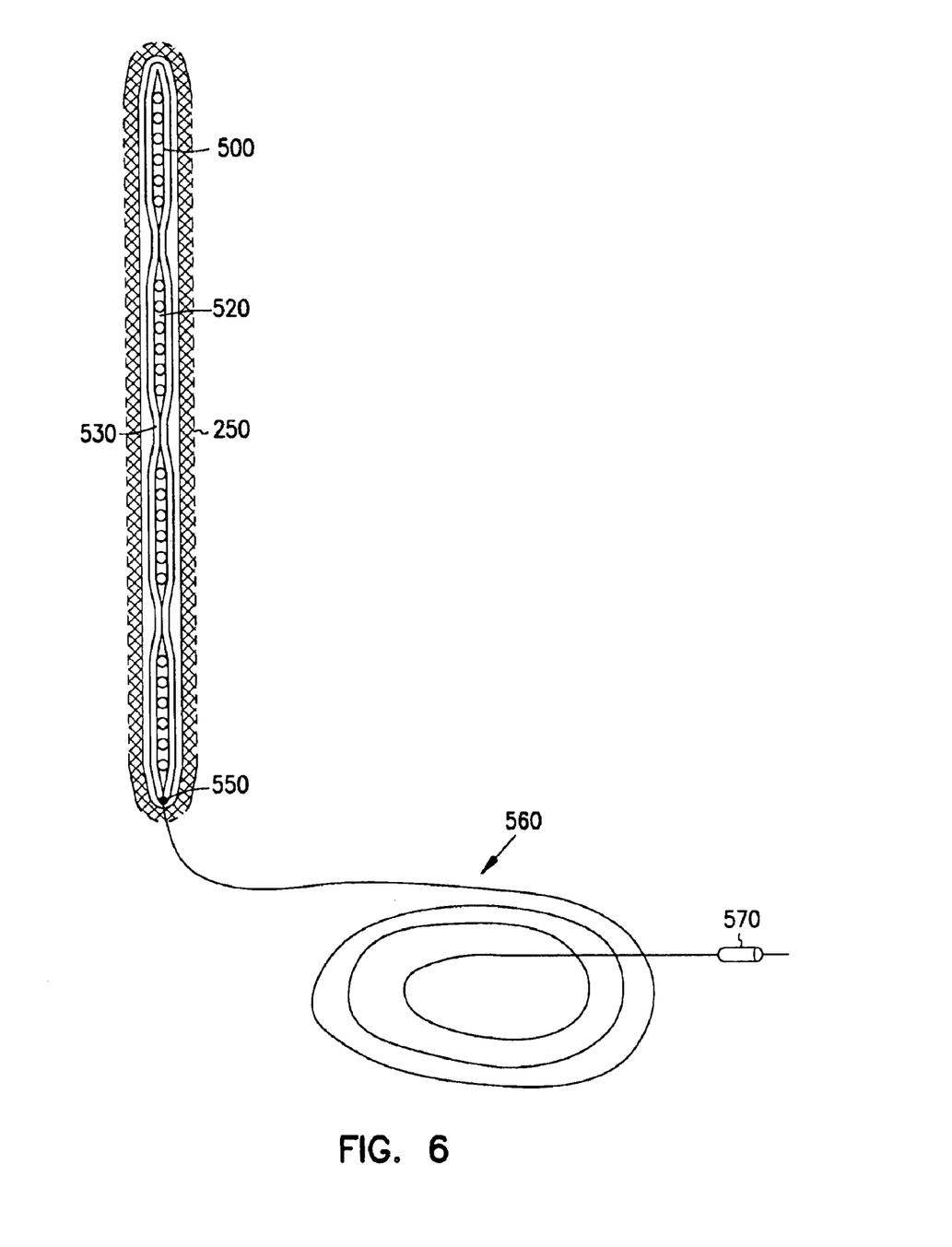
FIG. 6 is a side sectional view of one embodiment of the present subject matter, showing generally, the structure of first and second telemetry coils held in place by layers of a flexible housing.

FIG. 6 is a sectional view, similar to FIG. 3, illustrating generally, by way of example, not by way of limitation, another embodiment of housing two planarly concentrically wound telemetry coils 500 and 520 (e.g., first and second telemetry coils) captively held in place by layers of a flexible housing 530. Also shown in this embodiment, is a cable assembly 560 operatively coupled to the first and second telemetry coils 500 and 520 at 550 on first end and including an interface module 570 on the second end.

In one embodiment, the first and second telemetry coils are made by winding one or more loops of a conductive wire around a central core such that the one or more loops of conductive wire is substantially in a common plane having a constant gap between adjacent loops, and having an outside diameter ranging approximately between fifteen (15) to forty-six (46) centimeters.

Example Method of Using the Improved Inductive Coil Apparatus

FIGS. 1 and 4 illustrates generally, by way of example, not by way of limitation, one embodiment of portions of a biomedical telemetry device and an environment in which it is used. In one embodiment, a padded cover 250 is disposed over the telemetry coil assembly 110 including the first telemetry coil 210 having a cable assembly 150. A sterile cover (not shown for clarity) is disposed over the padded cover 250 including the telemetry coil assembly 10. The telemetry coil assembly 110 including the padded cover 250, and the sterile cover is disposed between the back of a patient's body (posterior location on a torso) and a common examination surgical furnishing 140. The cable assembly 150 is coupled to medical device programmer 160 using the interface module 240 for programming the patient's implanted medical device to provide device therapies and for monitoring the device.

In one embodiment a first telemetry coil 210 of a predetermined outer dimension sufficient to allow communication between the first telemetry coil 210 positioned at a posterior location of the torso and an implanted medical device 130 disposed subcutaneously on an anterior location of the torso is placed between the back of a patient and the examination table 140 to program the implanted medical device 130 using a medical device programmer 160.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

CONCLUSION

The above-described apparatus provides, among other things, a more even and large flux paths, which allow for robust performance in spite of less precise positioning of the telemetry apparatus with respect to an implanted medical device during a telemetry session. The large flux paths even permit placing the telemetry apparatus on the opposite side of the patient's body from the implanted medical device, or elsewhere around the patient.

It is understood that more telemetry coils than described above can be used to optimize multiple parameters for separate transmission and reception performance needs. It is also understood that the shape of telemetry coil can be other than what is described above. It is also understood by those skilled in the art, that the number of windings chosen for the telemetry coil can be determined by the required flux aperture area for any given application. It is also understood that increasing the number of windings will increase the size of the telemetry coil, which in turn increases the flux aperture area. It is also further understood that the initial surgical procedure to implant the medical device requires the telemetry coil assembly to enter the sterile surgical field for initial therapy programming and operational checkout. Thus, encasement assemblies could be made sterilizable or have sterilized and disposable coil assembly covers available for such procedures.

It is also to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A telemetry coil for communicating with an implanted medical device, comprising: a plurality of loops of a conductive wire that define a predetermined outer dimension sufficient to allow communication between the telemetry coil and the medical device, where the predetermined outer dimension is a diameter in a range of fifteen (15) to forty-six (46) centimeters, where the plurality of loops of a conductive wire wound substantially in a common plane and concentrically around a central core, where the central core includes a magnetically permeable material, and where the loops are positioned around the central core to form a substantially constant gap between adjacent loops.

2. The apparatus of claim 1, further including a flexible housing, where the flexible housing encases telemetry coil.

3. The apparatus of claim 2, where the flexible housing is conformable to an irregular surface.

4. The apparatus of claim 2, where the flexible housing is constructed of an insulating material.

5. The apparatus of claim 2, where the flexible housing is constructed of a material, which retains a formed shape.

6. The apparatus of claim 5, where the material is polyimide.

7. The apparatus of claim 2, further including:
 a flexible housing;
 a first telemetry coil; and
 a second telemetry coil, where the first telemetry coil and the second telemetry coil are concentrically positioned in a common plane within the flexible housing.

8. The apparatus of claim 2, further including a padded cover disposed over the flexible housing.

9. The apparatus of claim 1, where the magnetically permeable material is made of a ferrite powder.

10. An apparatus for communication with an implantable medical device, comprising:
 a first and a second telemetry coil, where the first and the second telemetry coil include a predetermined outer dimension sufficient to allow communications between the first and the second telemetry coils and the implantable medical device where the first and the second telemetry coils include one or more loops of a conductive wire, and wherein the first telemetry coil and the second telemetry coil are concentrically planarly wound substantially in a common plane, where the conductive wire is wound around a core, where the conductive loops are positioned around the central core to form a substantially constant gap between adjacent loops, where the core is constructed of a magnetically permeable material that enhances flux density of the apparatus, where the magnetically permeable material includes a ferrite powder; and
 a communication lead having a first end and a second end, where the first end is communicatively coupled to the first and the second telemetry coil and the second end adapted to be communicatively coupled to a medical device programmer.

11. The apparatus of claim 10, where the predetermined outer dimension is a diameter in a range of fifteen (15) to forty-six (46) centimeters.

12. The apparatus of claim 10, further comprising:
 a flexible housing, where the flexible housing encases the first and the second telemetry coil, where the flexible housing is conformable to an irregular surface.

13. The apparatus of claim 12, where the flexible housing is constructed of an insulating material.

14. An apparatus for communication with an implanted medical device, comprising:
 a first and a second telemetry coil concentrically planarly wound substantially in a common plane and each adapted to inductively couple with the implanted medical device, where the second telemetry coil is constructed and arranged to operate at a different telemetry operational frequency than the first telemetry coil; and
 a communication lead having a first end and a second end, where the first end is communicatively coupled to the first and the second telemetry coil and the second end is adapted to be communicatively coupled to a medical device programmer.

* * * * *